United States Patent [19]

Sela et al.

[11] Patent Number: 4,751,064
[45] Date of Patent: Jun. 14, 1988

[54] SYNTHETIC CHOLLERA VACCINE

[75] Inventors: Michael Sela; Ruth Arnon, both of Rehovot; Chaim O. Jacob, Petach Tikva, all of Israel

[73] Assignee: Yeda Research & Development Co., Ltd., Rehovot, Israel

[21] Appl. No.: 643,622

[22] Filed: Aug. 23, 1984

[30] Foreign Application Priority Data

Aug. 23, 1983 [IL] Israel .................................... 69558

[51] Int. Cl.$^4$ .................................... A61K 39/02
[52] U.S. Cl. ........................................ 424/92; 424/88; 514/837; 530/326
[58] Field of Search .................... 260/112.5 R, 112 R; 424/92, 88

[56] References Cited

U.S. PATENT DOCUMENTS

| | | | |
|---|---|---|---|
| 4,125,492 | 11/1978 | Cautricasas et al. | 424/92 |
| 4,411,888 | 10/1983 | Rlipstein et al. | 424/88 |
| 4,479,940 | 10/1984 | Bizzini | 260/112 R |

FOREIGN PATENT DOCUMENTS

| | | |
|---|---|---|
| 0095426 | 11/1983 | European Pat. Off. |
| WO83/00018 | 6/1983 | PCT Int'l Appl. |

OTHER PUBLICATIONS

Delbendi et al., Approach to a Synthetic Vaccine Against Cholera, C.A. No. 70627n (vol. 101) 1984.
Lai, Determination of the Primary Structure of Cholera Toxin B Subunit; JBC 252(20) 1977, pp. 7249–7256.
Mekalanso et al., Cholera Toxin Gene, C.A. No. 62626a, vol. 100, 1983.
Klipstein et al., Properties of Synthetically Produced E coli LT Infertion Immunity 39(1) 1983, pp. 117–121.
Hopp et al. "Prediction of Protein Antigenic Determi-ment of Amino Acid Sequence" PNAS 78(6) 1981, pp. 3824–3828.
Yamamoto et al., Primary Structure of Heat–Coiled: Enterotoxin Produced by E coli . . . Human" JBC 259(80) 1984, p. 5037.
Klipstein et al., Immunity & Inf. 39(1) 1983, p. 117.
CA. #134405k, vol. 94, 1981, Amino Acid Sequence Homolopy between Cholera Toxin and . . . Toxin.
Wolf, Marc et al., "Structure-Function Studies of Cholera Toxin and Its A and B", The Journal of Biological Chemistry, vol. 256, No. 11 (1981).
Duffy, Lawrence, et al., "Involvement of Arginine Residues in the Binding Site of Cholera Toxin Subunit B", Biochemical and Biophysical Research Communications, Dept. of Physiological Chem. and Pharm, Roche Institute of Molecular Biology, Nutley, N.J. 07110, vol. 91, No. 3, (1979).
Arnon, Ruth, et al., "Studies on the Chemical Basis of the Antigenicity of Proteins", J. Biochem., Department of Biophysics, The Weizmann Institute of Science, Rehovoth, Israel (1960).

Primary Examiner—John Kight
Assistant Examiner—Garnette D. Draper
Attorney, Agent, or Firm—Browdy and Neimark

[57] ABSTRACT

A synthetic vaccine against cholera and against heat-labile toxin of E. coli comprising a conjugate of a high-molecular weight carrier with a synthetic polypeptide corresponding to part of the sequence of Subunit B of natural cholera toxin. The sequences of choice are those corresponding to sequences 45 to 64, 50 to 64 and 8 to 20 of Subunit B, or slightly modified sequences, similar to the above.

6 Claims, 3 Drawing Sheets

Primary Structure of Subunit B

```
                                          10
Thr - Pro - Gln - Asn - Ile - Thr - Asp -Leu -Cys -Ala -Glu -Tyr -His -Asn-
                      20
Thr- Gln - Ile - His - Thr-Leu -Asn- Asn-Lys- Ile - Phe- Ser- Tyr-Thr-
       30                              40
Glu- Ser -Leu - Ala - Gly-Lys- Arg - Glu -Met -Ala- Ile - Ile -Thr-Phe-
                                 50
Lys-Asn- Gly - Ala - Thr-Phe- Glu- Val - Glu- Val - Pro- Gly- Ser- Gln-
         60                                      70
His-Ile - Asp- Ser- Gln -Lys- Lys- Ala - Ile -Glu- Arg-Met- Lys-Asn-

80
Thr-Leu- Arg - Ile - Ala -Tyr- Leu- Thr - Glu-Ala- Lys- Val -Glu-Lys-
                    90
Leu -Cys- Val - Trp- Asn-Asn- Lys- Thr- Pro -His -Ala- Ile - Ala- Ala-
  100            103
Ile - Ser -Met- Ala - Asn
```

Fig. 1

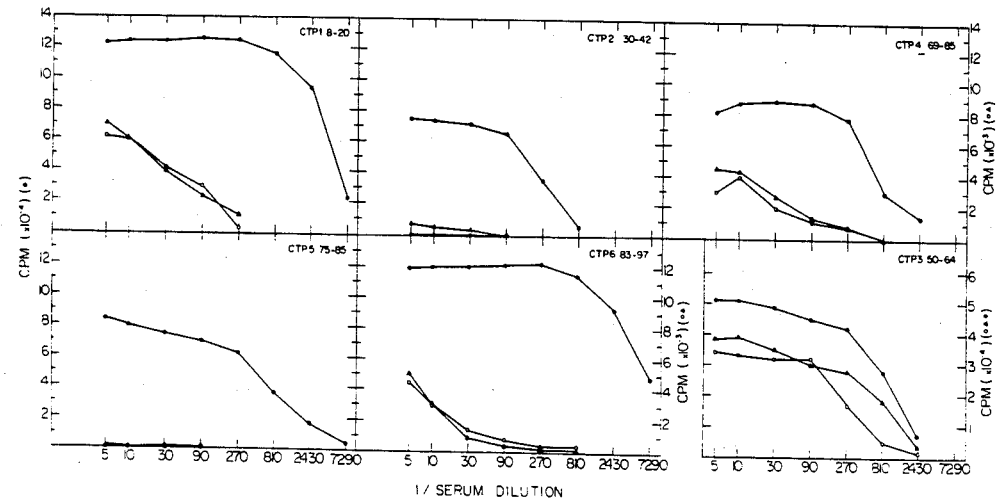

Fig. 2

400
SYNTHETIC CHOLLERA VACCINE

FIELD OF THE INVENTION

The invention relates to vaccines, adapted to induce selective immunity against cholera toxins (CT) and against heat labile toxin of *E. Coli* (LT of *E. Coli*). The vaccines are based on a combination of a high-molecular-weight moiety conjugated with a synthetic polypeptide which corresponds to a certain relatively short part of the B subunit of natural toxin. Polypeptides of choice are those corresponding to sequence 50 to 64, 8 to 20 and 45–64 of the natural B subunit of cholera toxin. The carrier can be a suitable toxoid, such as tetanus toxoid, or a synthetic polymeric carrier of adequate molecular weight, such as Poly AL (an alaninelysin polymer) of a molecular weight of at least about 50,000 and preferably in the 100,000 range.

The polypeptide can be synthesized by conventional methods of polypeptide synthesis such as solid phase synthesis according to Merrifield.

Antisera to the sequence 50 to 64 neutralize in a significant manner the biological activity of cholera toxin and also of heat labile toxin of E. Coli.

BACKGROUND TO THE INVENTION

Suitable synthetic peptides, attached to appropriate carriers, lead to antibodies capable of cross-reacting with proteins containing the peptides in their sequences. This has been shown to be true for hen egg-white lysozyme, for the coat protein of the bacteriophage MS2, and for influenza hemagglutin. Similar results have been reported on protein M of *Streptococcus pyogenes*, diphtheria toxin hepatitis virus, and foot and mouth disease virus. In several cases of viruses and toxins, the antibodies formed were capable of neutralizing the biological activities.

The purpose of the present invention is to provide synthetic peptides capable of provoking antibodies neutralizing efficiently cholera toxin and other similar toxins, such as heat-labile toxin of *E. Coli*.

The toxin of Vibrio cholerae is composed of two subunits, A and B.

Subunit A activates adenylate cyclase which triggers the biological activity, whereas subunit B is responsible for binding to cell receptors, and expresses most immunopotent determinants. Antibodies to the B subunit are capable of neutralizing the biological activity of the intact toxin. The B subunit (choleragenoid) is a pentamer, each of the chains containing 103 amino acid residues.

The invention relates to the synthesis of several peptides derived from the B subunit of the cholera toxin, and to antibodies neutralizing the intact cholera toxin as well as other toxins, such as heat-labile toxin of *E. Coli*.

SUMMARY OF THE INVENTION

There are provided synthetic vaccines against cholera toxins and against heat-labile toxin of *E. Coli*. These comprise a suitable polypeptide, corresponding to a predetermined part of the B subunit of cholera toxin, conjugated to a suitable polymeric high molecular weight carrier, such as a suitable toxoid (tetanus toxoid or the like) or to a suitable polymer, such as Poly AL of a molecular weight of at least about 50,000 and preferably in the 100,000 to 120,000 range.

The synthetic polypeptides of choice are either the one corresponding to sequence 50 to 64, to the sequence 45 to 64, or to sequence 8 to 20 of the B subunit of cholera toxin. The 50 to 64 sequence unit has the composition, Val-Glu-Val-Pro-Gly-Ser-Gln-His-Ile-Asp-Ser-Gln-Lys-Lys-Ala, while the 8 to 20 sequence has the composition, Leu-Cys-Ala-Glu-Tyr-His-Asn-Thr-Gln-Ile-His-Thr-Leu.

The sequence 45–64 has the composition, Gly-Ala-Thr-Phe-Glu-Val-Glu-Val-Pro-Gly-Ser-Gln-His-Ile-Asp-Ser-Gln-Lys-Lys-Ala.

In the 50 to 64 sequence it is possible to substitute instead of the N-terminal Val any other amino acid. Instead of the C-terminal Ala there can be inserted Cys, and such modified polypeptides will have a similar activity, or even a more pronounced one.

In the 8–20 sequence there can be inserted instead of Cys the Ala amino acid and a similar activity is obtained. This was established by experimental work.

It is clear that slight modifications of the above defined sequences can be resorted to, both as regards chain length and composition, without departing from the scope and spirit of the invention.

The polypeptide must be conjugated to a suitable carrier of adequate molecular weight in order to be able to induce antibody formation.

Tetanus toxoid has been found to be a suitable carrier. There may also be used any suitable polymer, preferably based on amino acids, such as Poly AL (an alaninelysin copolymer) of the range of average M.W. of about 100,000 to 120,000. It seems that a MW of at least 50,000 is required.

The invention is illustrated in the following with reference to certain specific embodiments, which ought to be construed in a non-limitative manner.

The synthetic vaccines have been found to be effective also against heat-labile toxin of *E. Coli* (LT of *E. Coli*).

Antibodies against the two peptides neutralize the activity of LT of *E. Coli* in the same manner as cholera toxin (CT). The third polypeptide, of sequence 45 to 64 has a slightly better activity than that of sequence 50–64. There was tested the cross-reaction of anti-(8-20-polypeptide) and anti-(50-64-polypeptide) with LT of *E. Coli* in a radioimmunoassay and in an immunoblotting test; they were found to be cross-reactive. Neutralization of LT-*E. Coli* prevents adenylate cyclase activity induced by the toxin. It prevents secretion of fluid into ligated ileal loops of rat intestine; it prevents cholera toxin induced adenylate cyclase activity.

DESCRIPTION OF THE PREFERRED EMBODIMENT

Cholera toxin was purchased commercially. Separation of subunits and isolation of the B subunit were performed by gel filtration of Sephadex G-75 in 5% formic acid, according to Lai, C. Y. (1980) CRC Critical Reviews in Bioch 9, 171–207, t-Butyloxycarbonyl (t-boc) derivatives of the various amino acids were purchased commercially. All other reagents were of analytical grade or the best grade available.

PEPTIDE SYNTHESIS

Peptides were synthesized by solid phase method according to Merrifield, B. B. (1965) Sci 150, 178–185. The side chain protecting groups of the t-boc derivatives were as follows: benzyl ethers for the hydroxyls of serine and threonine, dichlorobenzyl ether for the phenolic hydroxyl of tyrosine, and carbobenzoxy for the ε-amino group of lysine. Asparagine and glutamine were protected at the α-carboxyl group by p-nitrophenyl ester. The nitroguanidino group of arginine and the imidazole group of histidine were protected by tosyl. The initial amino acid-resin was prepared by esterification of the relevant t-boc-amino acid to chloromethylated resin (polystyrene-1% divinylbenzene).

The progress of synthesis was monitored by ninhydrin analysis. Two cycles of coupling were performed whenever coupling reaction was less than $\geq 99\%$ complete by ninhydrin test and amino acid analysis. For the synthesis of CTP 6 5% (v/v) 1,2-ethanedithiol was added to the trifluoroacetic acid to prevent oxidation of tryptophan. The protecting groups were removed and the peptides were cleaved from the resin at 0° C. with anhydrous hydrogen fluoride containing 10% anisole and 1% 1,2 ethanedithiol as scavengers.

Crude peptides recovered after cleavage from the resin were purified on Sephadex G-25 column. Purity of peptides was analyzed by amino acid analysis, by reverse-phase HPLC and/or high voltage papaer electrophoresis.

CONJUGATION OF PEPTIDES WITH TETANUS TOXOID

Two methods of conjugation were used:

(I) 1-Ethyl-3-(3'-dimethylaminopropyl)carbodiimide hydrochloride as the coupling agent as described previously, Muller et al. (1982) Proc. Nat. Acad. Sci. USA 79, 569-573.

(II) While still on the resin, the peptide was elongated by t-boc p-aminophenylacetic acid (PAPA) prior to the HF cleavage. PAPA peptides were dissolved in cold 2N HCl, diazotized by addition of ice cold aqueous sodium nitrite (0.1M), and added to a solution of tetanus toxoid in $NaHCO_3$(0.5M), while maintaining pH 8.5 by addition of concentrated $Na_2CO_3$. After 10 hours at 4° C., the mixture was dialysed against 10 mM ammonium carbonate and lyophilized. The peptide content of the conjugates was determined by amino acid analysis and by trace labelling with $^{125}I$, when possible.

IMMUNIZATION PROCEDURE

Rabbits were immunized by multisite intradermal injections of 1 mg of conjugate dissolved in 0.5 ml of Pi/NaCl and emulsified in 0.5 ml of complete Freund's adjuvant, with several boosters, as described previously, Müller et al. (1982) Proc. Nat. Acad. Sci. USA 79, 569-573.

Solid Phase Radioimmunoassay (RIA) was performed on antigen-coated (0.5-1.0 μg/well) V-bottom flexible microtiter plates (precoated with glutaraldehyde (0.2%) whenever peptides were used as antigen) by addition of three-fold serial dilution of the tested serum, followed by $^{125}I$ protein A labelled by Bolton and Hunter reagent ($10^5$ cpm/50 μl/well). The washed and dried wells were cut and counted in a gamma counter.

In competitive inhibition assays the antigen coated wells were incubated with 10 fold serial dilutions of the tested inhibitor peptide solution in Pi/NaCl containing 0.1% BSA, prior to addition of a constant dilution of the antipeptide serum.

Enzyme Labelled Immunosorbent Assay (ELISA) was carried out similarly to the RIA, except that flat bottom plates were used, and a β-galactosidase conjugate of protein A (Amersham) was used instead of the radioactive label. After addition of the substrate (O-nitrophenyl-β-Δgalactopyranoside), the plates were read in an automatic reader.

IMMUNOPRECIPITATION

Cholera toxin was labelled with $^{125}I$ by the chloramine-T method. Immunoprecipitation was performed basically according to Kessler Heitmancik et al., (1977) Infect. Immun., 17, 621-628. Immunoprecipitation was performed basically according to Kessler, S. W. (1975) J. Immunol. 115, 1617-1624, with slight modifications. $^{125}I$-Labelled cholera toxin was preadsorbed on intact Staphylococcus A and then reacted with various antisera. The precipitates obtained after addition of fixed Staphylococcus A were analyzed by 5-15% NaDodSO₄ polyacrylamide gel electrophoresis and visualized by autoradiography.

ELECTROPHORETIC BLOTTING PROCEDURE

Cholera toxin, separated into its subunits on a 5-15% $NaDodSO_4$ poly-acrylamide gel, was transferred to nitrocellulose sheet according to the method of Towbin et al. (1979) Proc. Natl. Acad. Sci. USA 76, 4350-4354. To reduce nonspecific binding of antiserum, the blot was incubated for 1 hr with 9 mM Tris HCl buffer, pH 7.4, containing 0.9M NaCl and 3% w/v BSA, and then cut into strips. The strips were incubated for 3 hr at room temperature with 1:50 dilution of different antisera.

After thorough washing, the strips were incubated for 2 hours with $^{125}I$-labelled goat anti-rabbit IgG ($5 \times 10^5$ cpm/ml). The washed and dried blots were autoradiographed.

TOXIN NEUTRALIZATION ACTIVITY (I) Vascular permeability assay

The assay was performed essentially according to Craid, J. P. (1966) J. Bacterial. 92, 795, and Lai, C. Y. (1980) CRC Critical Reviews in Biochem, 9, 171-207 with slight modifications:

Serial dilutions of the test antisera were mixed with a constant amount of cholera toxin, incubated for 1 hour at room temperature and 0.1 ml of the mixtures were injected intradermally in triplicates into the shaved skin of adult rabbit. After 18 hours the rabbit was injected I.V. with 1 ml/kg of 5% Evans Blue and the diameter of the resulting blue induration was measured 1 hour later. Neutralization end point was taken to be the highest dilution of serum which prevented the blueing phenomenon. Both positive (no antiserum) and negative (no cholera toxin) controls were included in each rabbit.

(II) The ligated ileal loop assay The assay was performed essentially as described by Fujita and Finkelstein (1972) J. Infect. Dis. 125, 647-655. Briefly, rats or adult rabbits fasted for 12 hours were anesthesized with ether, the abdomen opened, and the small intestine ligated in 3-4 cm long loops starting approximately 10 cm from the duodenum. The loops were injected with different dilutions of the tested sera previously incubated with a constant amount of cholera toxin, and the abdomen closed. Food and water were withheld and the animals sacrificed after 5 hours. Fluid accumulation per centimeter of loop was determined by measuring the length and weight of each loop. Both positive (no antiserum) and negative (no cholera toxin) controls were included in each animal.

CLEAVAGE OF B SUBUNIT

To locate the regions participating in antigenic reactivity, the B subunit was cleaved by CNBr to yield three fragments with the following sequences: 1-37 and 69-101 linked by a disulfide bridge between cysteine residues at positions 9 and 86; 36-68 and 102-103. The fragments were separated on a Sephadex G-50 column, and the two larger peptides were tested for reactivity with antisera prepared against cholera toxin. The largest peptide was partially cross reactive with anti cholera toxin sera, whereas the peptide 38-68, although incapable of binding directly to the antisera, was capable of inhibiting the toxin-anti-toxin homologous anti-sera (results not shown).

SELECTION OF PEPTIDES FOR SYNTHESIS

Considerations based on the above results obtained with the cyanogen bromide fragment of B subunit, dictated the selection of peptides for chemical synthesis. Peptide 30-42 (CTP 2) was synthesized since it was suggested that Arg 35 or the region surrounding it may be involved in antibody and receptor binding activity, Duffy et al. (1979) Biochem. Biophys. Res. Comm. 91, 1005-1010. Peptide 83-97 (CTP 6) containing tryptophan at position 88 was synthesized, since chemical modification of this residue had resulted in loss of GM1 binding to cholera toxin, De Wolf et al. (1981) J. Biol. Chem. 256, 5481-5488. We have also synthesized the peptide containing the hightest local average hydrophilicity (residues 79-84), since such sequences are thought to be located in or immediately adjacent to antigenic determinants, Hoop et al. (1981) Proc. Natl. Acad. Sci. USA 78, 3824-3828. Based on the reported role of tyrosine residues for anti-genicity, Arnon et al. (1960) Biochem. J. 75, 103-109, peptides containing, respectively, Tyr 12 and Tyr 76, namely, CTP 1 (residues 8-20) and CTP 5 (residues 75-85) were included. Since the latter peptide contained only 11 residues, we prepared an additional peptide with a longer sequence (residues 69-85, denoted CTP 4). Peptide 50-64 (CTP 3) was synthesized since it is a part of the inhibitory CNBr fragment 38-68.

SYNTHESIS AND CONJUGATION OF PEPTIDES

The peptides synthesized correspond to several regions of the B subunit of cholera toxin (FIG. 1). The only change from the native sequence was the replacement of cysteines at position 9 and 86 (in CTP 1 and 6), respectively, by alanine to avoid formation of aggregates. The results of amino aid analyses of the peptides were in good agreement with the expected values for the various amino acid residues. The purity of the peptides was further established by reverse phase HPLC and/or high voltage paper electrophoresis, indicating less than 5% impurities in the end products. The purified peptides were conjugated to tetanus toxoid either using a water-soluble carbodiimide as a coupling agent, or through an azo bond, when PAPA derivatives of the peptides were employed. The advantage of binding via PAPA residue is the specificity of the conjugation which occurs only between the N-terminal amino group of the PAPA and histidine or tyrosine residues on the carrier, Spirer et al. (1977) Eur. J. Immunol. 7, 69-74. Both methods of coupling yielded adequate conjugates (Table 1).

IMMUNOLOGICAL REACTIVITY

The conjugates of tetanus toxoid with all six peptides induced antibodies specific towards the respective homologous peptide (FIG. 2). As shown, the highest response was observed with CTP 1 and CTP 6. Four of the antisera were also cross-reactive to a different extent with the intact B subunit and whole native cholera toxin. This cross-reactivity was demonstrated by three assays—by solid phase radioimmunoassay (FIG. 2), immuno-blotting technique (FIG. 3) and by immunoprecipitation (Table 2). All three methods showed similar results.

Peptides CTP 3 induced antibodies which gave a very strong cross-reactivity with the intact toxin, similar in its level to that of the homologous peptide antipeptide reaction (FIG. 2). Both the homologous peptide anti-peptide reaction and the cross-reactivity are indeed specific, since they can be completely inhibited by excess of the free CTP 3 peptide (FIG. 4). Furthermore, CTP 3 is the only peptide of those investigated which reacted with antiserum against the intact native cholera toxin (FIG. 5). Thus, the cross-reactivity with a native protein is not a characteristic of just any peptide segment derived from it.

This is further confirmed by a comparision of the related peptides CTP 4 (69-85) and CTP 5 (75-85). Antiserum against CTP 5 was incapable of cross-reacting with either B subunit or whole toxin, although it had a high titer towards the homologous peptide. Elongation of this peptide by 6 amino acid residues resulted in CTP 4, which elicited antibodies cross-reactive with the intact proteins, even though the homologous anti-peptide titer was not significantly hight than in the case of CTP 5.

The results of the immunoprecipitation experiment (Table 2) present the quantitative aspect of the cross-reactivity between the anti-peptides and cholera toxin. The anti-peptide CTP 3 indeed gives the highest cross-reactivity, amounting to about 30 percent of the homologous toxin-anti toxin reaction. In accordance with the results of the RIA, anti CTP 1 and CTP 6 are significantly cross-reactive with the intact toxin, whereas the remaining peptides show only slight reactivity. The immunoblotting experiment serves as another confirmation of these results, and raises an additional point of interest: since in this case the intact cholera toxin was separated by electrophoresis into its two subunits prior to the interaction with the various antisera, it is clear from the results (FIG. 3) that antiserum to CTP 1 reacts not only with the B subunit, but also, to an appreciable extent, with the A subunit of cholera toxin.

INHIBITION OF ADENYLATE CYCLASE ACTIVITY

Since the diarrhea occurring in response to CT or LT is a result of activation of the adenylate cyclase in the cell membrane of small intestinal epithelial cells, we have evaluated the capacity of the different antisera to inhibit CT-induced or LT-induced adenylate cyclase activity. The enzyme activity was determined by testing the level of cAMP production in dispersed kidney cells of chickens. As shown in Table 5, antisera to CTP1 and CTP3 specifically inhibit CT-induced adenylate cyclase activity up to about 60-65%. The same is true for CT induced adenylate cyclase activity, namely CTP1 and anti CTP3 specifically inhibit its activity to a similar extent.

NEUTRALIZATION OF BIOLOGICAL ACTIVITY

The sera against the various peptides were evaluated for their capacity to neuralize biological effects of cholera toxin. For this purpose, two in vivo assays of the cholera toxin activity, namely, a skin test measuring the increased vascular permeability induced by the toxin, as well as the fluid accumulation induced by cholera toxin in ligated small intestinal loops of adult rabbits, were employed. The results of these two experiments are presented in Tables 3 and 4. In both assays anti-CTP 3 caused partial inhibition of the toxin activity. Although less effective than antiserum against native cholera toxin, the anti-CTP 3 reduced quite significantly—up to 40%—the fluid accumulation in rabbit intestine. These two assays, alhough performed in vivo, demonstrate only the presence of antibodies in the sera of the immunized rabbits. Peptide CTP 3, which showed the strongest immunological cross-reaction with cholera toxin, has an appreciable ability to induce antibodies capable of neutralizing the biological activity of cholera toxin. It can be used for inducing protective immunity towards the toxin.

The above experiments indicate that the synthetic vaccines thus produced can be used for vaccination against cholera toxin. The required quantity of the polypeptide-carrier conjugate for vaccination of humans is in the range of about 2 to 20 mg.

It is clear that the conjugate has to be administered in a suitable carrier with suitable adjuvants.

BRIEF DESCRIPTION OF THE DRAWINGS

Reference is made to the enclosed drawings, in which:

FIG. 1 provides the amino acid sequence of subunit B of cholera toxin;

FIG. 2 illustrates the antibody response of rabbits to different peptides of subunit B of cholera toxin;

In the above Figures FIG. 2 illustrates the antibody response of rabbits to different peptides of the B subunit of cholera toxin. Reactions with: ●—homologous peptides; ▲—the B subunit of cholera toxin; and ○—cholera toxin. Note the difference in the scales of the reactions with the peptide and the intact proteins in the case of all peptides except CTP 3.

TABLE 1

Figure 3:
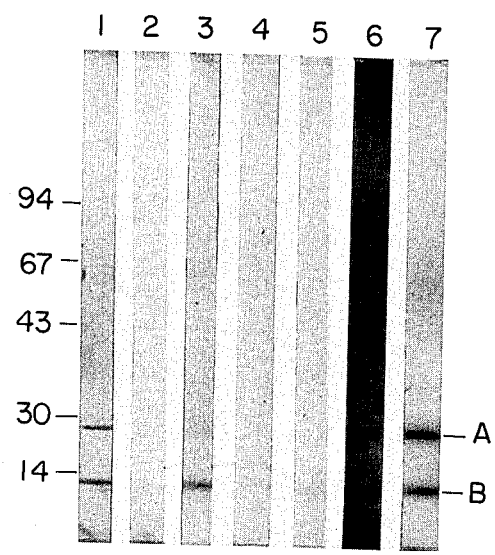
FIG. 3 illustrates the cross-reacativity of different peptides established by the immunoblotting technique.
Figure 4:
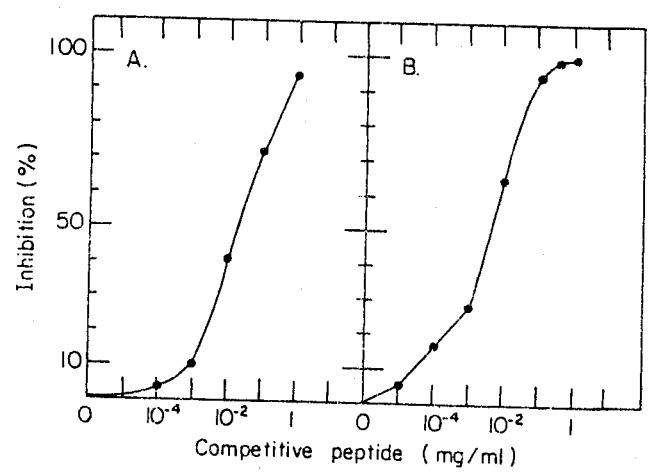
FIG. 4 illustrates the cross-reactivity of the peptides and the inhibition by one of the synthetic peptides.
Figure 5:
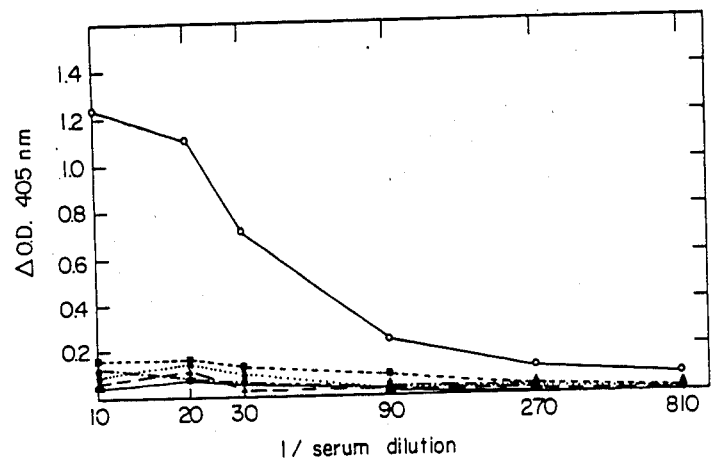
FIG. 5 illustrates the reactivity of the 50–64 peptide with antiserum against cholera toxin.

Properties of Various Peptide Conjugates with Tetanus Toxoid (MW 150,000)

| Peptide | Position | Method of coupling | Peptide/carrier ratio used for coupling (mol/mol) | Peptide/carrier ratio in the conjugate (mol/mol) |
|---|---|---|---|---|
| BP$_1$ | 8–20 | PAPA* | 95 | 54 |
|  |  | EDCl** | 40 | 27 |
| BP$_2$ | 30–42 | EDCl | 45 | 11 |
| BP$_3$ | 50–64 | PAPA | 94 | 63 |
|  |  | EDCl | 41 | 14 |
| BP$_4$ | 69–85 | EDCl | 40 | 19 |
| BP$_5$ | 75–85 | EDCl | 35 | 10 |
| BP$_6$ | 83–97 | PAPA | 75 | 25 |
|  |  | EDCl | 49 | 24 |

*PAPA = p-Aminophenylacetic acid, attached to the peptide via an amide bond, and coupled to the protein after diazotization.
**EDCl = 1-Ethyl-3-(3-dimethylaminopropyl) carbodiimide hydrochloride.

TABLE 2

Immunoprecipitation of $^{125}$I-Cholera toxin by different antipeptide sera

| Serum sample | $^{125}$I-Cholera toxin precipitated cpm | % of total radioactivity |
|---|---|---|
| anti CTP1 | 41880 | 4.4 |
| anti CTP2 | 9119 | 0.9 |
| anti CTP3 | 66498 | 7.0 |
| anti CTP4 | 4956 | 0.5 |
| anti CTP5 | 2980 | 0.3 |
| anti CTP6 | 47813 | 5.0 |
| anti cholera toxin | 221560 | 23.0 |
| preimmune serum | 2694 | 0.28 |

TABLE 3

Inhibition by anti CTP 3 peptide of cholera toxin-induced vascular permeability in rabbit skin

| Challenge (ng toxin) | Vascular permeability reaction$^a$ anti cholera toxin$^b$ | anti CTP 3$^b$ | preimmune serum$^b$ |
|---|---|---|---|
| 0.5 | — | — | +++ |
| 1.0 | — | + | +++ |
| 2.0 | — | +++ | +++ |
| 3.0 | — | +++ | +++ |

$^a$+++ strong blue induration
+ faint blue induration
— no blue colour
$^b$All sera were used at 1:10 dilution

TABLE 4

Neutralization of cholera toxin by antisera to peptide CTP 3 (50-64)

| Cholera toxin (μg) | Serum | Dilution | Ligated ileal loop Weight/cm loop (g) | Reduced secretion$^a$ (%) |
|---|---|---|---|---|
| 0.0 | none (saline) |  | 0.20 |  |
| 1.5 | none (saline |  | 1.30 | 40 |
| 1.5 | anti cholera toxin | 1:20 | 0.45 |  |
| 1.5 | anti-CTP 3 | 1:2 | 1.02 |  |
| 1.5 | normal rabbit serum | 1:2 | 1.25 |  |
| 3.0 | none (saline) |  | 1.36 | 33 |
| 3.0 | anti cholera toxin | 1:20 | 0.51 |  |
| 3.0 | anti-CTP 3 | 1:2 | 1.08 |  |
| 5.0 | none (saline) |  | 1.42 | 12 |
| 5.0 | anti cholera toxin | 1:20 | 0.58 |  |
| 5.0 | anti-CTP 3 | 1:2 | 1.32 |  |
| 7.5 | none (saline) |  | 1.42 | 12 |
| 7.5 | anti cholera toxin | 1:20 | 0.60 |  |
| 7.5 | anti-CTP 3 | 1:2 | 1.32 |  |
| 10.0 | none (saline) |  | 1.50 | 0 |
| 10.0 | anti cholera toxin | 1:20 | 0.69 |  |
| 10.0 | anti-CTP 3 | 1:2 | 1.50 |  |

$^a$Assuming that the reduction effected by antiserum to cholera toxin is 100%.

TABLE 5
Specificity of cAMP inhibition by antisera.

| Antiserum added | Cyclic AMP induced by: | | | | | | |
|---|---|---|---|---|---|---|---|
| | Chloera toxin | | | Parathyroid hormone | | Isoproterenol | |
| | pmoles/ 250000 cells | % | Significance (p)[a] | pmoles/ 250000 cells | % | pmoles/ 250000 cells | % |
| None | 5.9[b] | 100 | | 3.7 | 100 | 4.8 | 100 |
| NRS | 5.6 | 95 | n.s.[c] | 3.5 | 94 | 4.6 | 95 |
| CT | 0.5 | 8 | 0.001 | 3.8 | 100 | 4.6 | 95 |
| CTP1 | 3.2 | 54 | 0.01 | 3.7 | 100 | 4.7 | 98 |
| CTP3 | 2.5 | 42 | 0.01 | 3.5 | 94 | 4.6 | 95 |
| TT | 5.6 | 95 | n.s. | n.t.[d] | | n.t. | |

[a]Significance of the difference between cholera toxin induced cAMP without antiserum and with any of the antisera used.
[b]Values represent mean of 3 experiments.
[c]n.s. — Not significant
[d]n.t. — Not tested.

We claim:

1. A synthetic vaccine against cholera and against heat-labile toxin of *E. Coli*, comprising a vaccine-effective amount of a conjugate of a high-molecular weight carrier having a molecular weight of at least 50,000, with a synthetic polypeptide corresponding to a part of the sequence of Subunit B of natural cholera toxin selected from the group consisting of the sequence of the cholera toxin of 50–64, 50–64 wherein the N-terminal Val is substituted by another amino acid, 50–64 wherein the C-terminal Ala is substituted by Cys, and 50–64 wherein the N-terminal Val is substituted with another amino acid and the C-terminal Ala is substituted with Cys, and a suitable adjuvant or diluent.

2. A vaccine according to claim 1, wherein the sequence corresponds to that of sequence 50 to 64 of the cholera toxin.

3. A vaccine according to claim 1, wherein the high molecular weight carrier is tetanu toxoid.

4. A vaccine according to claim 1, wherein the high molecular weight carrier is a polymer of the type POLY AL of an average molecular weight of at least 50,000.

5. A vaccine according to claim 1 wherein the high molecular weight carrier has a molecular weight of about 100,000–120,000.

6. A synthetic vaccine against cholera and against heat-labile toxin of *E. Coli*, comprising a vaccine-effective amount of a conjugate of a high-molecular weight carrier having a molecular weight of at least 50,000, with a synthetic polypeptide corresponding to a part of the sequence of Subunit B of natural cholera toxin selected from the group consisting of substantially sequences of the cholera toxin of 50–64 and; a suitable adjuvant or diluent.

* * * * *